(12) United States Patent
Naoe et al.

(10) Patent No.: US 7,314,862 B2
(45) Date of Patent: Jan. 1, 2008

(54) ANTITUMOR AGENT

(75) Inventors: Yoshinori Naoe, Yokohama (JP); Yuka Sasakawa, Osaka (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 10/948,288

(22) Filed: Sep. 24, 2004

(65) Prior Publication Data
US 2005/0070467 A1 Mar. 31, 2005

(30) Foreign Application Priority Data
Sep. 25, 2003 (JP) ............................ 2003-334340
Oct. 2, 2003 (JP) ............................ 2003-344315

(51) Int. Cl.
*A61K 38/12* (2006.01)
*A61K 38/00* (2006.01)
*A61K 38/02* (2006.01)
*C07K 5/12* (2006.01)
*C07K 2/00* (2006.01)

(52) U.S. Cl. .............................. 514/9; 514/2; 530/300; 530/317

(58) Field of Classification Search .................. 514/9; 530/317
See application file for complete search history.

(56) References Cited

U.S. PATENT DOCUMENTS

| | | | | | |
|---|---|---|---|---|---|
| 486,379 | A | * | 11/1892 | King ............................... | 54/30 |
| 574,455 | A | * | 1/1897 | Schrantz ....................... | 246/448 |
| 3,997,633 | A | * | 12/1976 | Leva et al. ................... | 261/113 |
| 4,348,388 | A | * | 9/1982 | Garland et al. ............... | 514/34 |
| 4,401,592 | A | * | 8/1983 | Yoshikumi et al. ......... | 424/181.1 |
| 4,950,755 | A | * | 8/1990 | Witiak et al. ................ | 544/82 |
| 4,977,138 | A | | 12/1990 | Okuhara et al. | |
| 5,091,373 | A | * | 2/1992 | Gatti et al. .................... | 514/34 |
| 5,242,901 | A | * | 9/1993 | Speyer et al. .................. | 514/8 |
| 5,514,664 | A | * | 5/1996 | Ulrich .......................... | 514/34 |
| 5,620,961 | A | * | 4/1997 | Markovic et al. ............ | 514/23 |
| 5,780,054 | A | * | 7/1998 | Tardi et al. ................... | 424/450 |
| 5,919,816 | A | * | 7/1999 | Hausheer et al. ............ | 514/449 |
| 6,020,373 | A | * | 2/2000 | Schellenberg et al. ....... | 514/459 |
| 6,197,809 | B1 | * | 3/2001 | Strelchenok ................ | 514/459 |
| 6,286,513 | B1 | * | 9/2001 | Au et al. ..................... | 128/898 |
| 6,348,209 | B2 | * | 2/2002 | Placke et al. ................ | 424/435 |
| 6,403,555 | B1 | | 6/2002 | Skov | |
| 6,419,900 | B2 | * | 7/2002 | Placke et al. .................. | 424/45 |
| 6,419,901 | B2 | * | 7/2002 | Placke et al. .................. | 424/45 |
| 6,451,784 | B1 | * | 9/2002 | Placke et al. ................ | 514/184 |
| 6,471,943 | B1 | * | 10/2002 | Placke et al. .................. | 424/45 |
| 6,541,661 | B1 | * | 4/2003 | Delorme et al. ............ | 560/318 |
| 6,800,639 | B2 | * | 10/2004 | Giles et al. ................... | 514/300 |
| 6,905,669 | B2 | | 6/2005 | DiMartino | |
| 7,056,883 | B2 | | 6/2006 | Ito et al. | |
| 7,056,884 | B2 | | 6/2006 | Nakajima et al. | |
| 2001/0018425 | A1 | * | 8/2001 | Strelchenok ................. | 514/34 |
| 2001/0036444 | A1 | * | 11/2001 | Placke et al. .................. | 424/43 |
| 2001/0038826 | A1 | * | 11/2001 | Placke et al. .................. | 424/43 |
| 2001/0038827 | A1 | * | 11/2001 | Placke et al. .................. | 424/43 |
| 2002/0028237 | A1 | * | 3/2002 | Colbern et al. ............. | 424/450 |
| 2002/0049169 | A1 | * | 4/2002 | Minotti et al. ................ | 514/34 |
| 2002/0049170 | A1 | * | 4/2002 | Minotti et al. ................ | 514/34 |
| 2002/0131995 | A1 | * | 9/2002 | Szoka, Jr. .................... | 424/450 |
| 2002/0155066 | A1 | * | 10/2002 | Placke et al. .................. | 424/43 |
| 2002/0156023 | A1 | * | 10/2002 | Walling et al. ............... | 514/27 |
| 2002/0192814 | A1 | * | 12/2002 | Tamarkin et al. ......... | 435/320.1 |
| 2003/0053983 | A1 | * | 3/2003 | Tamarkin et al. .......... | 424/85.1 |
| 2003/0083316 | A1 | * | 5/2003 | Giles et al. .................... | 514/86 |
| 2003/0099960 | A1 | * | 5/2003 | Ratain et al. .................. | 435/6 |
| 2003/0144570 | A1 | * | 7/2003 | Hunter et al. .................. | 600/1 |
| 2003/0166602 | A1 | * | 9/2003 | Szoka, Jr. ..................... | 514/44 |
| 2004/0014694 | A1 | * | 1/2004 | Chakroun .................... | 514/34 |
| 2004/0053820 | A1 | | 3/2004 | Nakajima et al. | |
| 2004/0077561 | A1 | * | 4/2004 | Minotti et al. ................ | 514/34 |
| 2004/0136905 | A1 | * | 7/2004 | Kent et al. .................. | 424/1.11 |
| 2004/0152632 | A1 | * | 8/2004 | Feingold ...................... | 514/12 |
| 2005/0004081 | A1 | * | 1/2005 | Giles et al. .................... | 514/86 |
| 2005/0070467 | A1 | | 3/2005 | Naoe et al. | |
| 2005/0187149 | A1 | | 8/2005 | Naoe et al. | |
| 2005/0191713 | A1 | | 9/2005 | Sasakawa et al. | |
| 2005/0222013 | A1 | | 10/2005 | Jung et al. | |
| 2006/0135413 | A1 | | 6/2006 | Naoe et al. | |
| 2006/0223747 | A1 | | 10/2006 | Ito et al. | |

FOREIGN PATENT DOCUMENTS

| | | | |
|---|---|---|---|
| EP | 1 302 476 | A1 | 4/2003 |
| EP | 1426054 | A1 * | 6/2004 |
| WO | WO 02/06307 | | 1/2002 |
| WO | WO 02/085400 | A1 | 10/2002 |
| WO | WO 03015810 | A1 * | 2/2003 |
| WO | WO 2004/064727 | A2 | 8/2004 |
| WO | WO 2004/103358 | A2 | 12/2004 |
| WO | WO 2004/103369 | A1 | 12/2004 |

OTHER PUBLICATIONS

R. Furumai, et al. Cancer Res. (2002), pp. 4916-4921.*
H.J. Kwon, et al. Int. J. Cancer (2002), pp. 290-296.*
W.-G. Zhu and G.A. Otterson. Curr. Med. Chem. (2003), pp. 187-199.*
M. Murata, et al. Jpn. J. Cancer. Res. (2000), pp. 1154-1160.*
Y. Sasakawa, et al. Cancer Letters. (2003), pp. 161-168.*
Y. Sasakawa, et al. Biochem. Pharm. (2003), pp. 897-906.*

(Continued)

*Primary Examiner*—Cecilia J. Tsang
*Assistant Examiner*—Andrew D. Kosar
(74) *Attorney, Agent, or Firm*—Oblon, Spivak, McClelland, Maier & Neustadt, P.C.

(57) ABSTRACT

The present invention relates to an antitumor agent containing a histone deacetylase inhibitor and a topoisomerase II inhibitor in combination. This combination has been found to exhibit a synergistic anticancer or antitumor effect compared to administration of either the histone deacetylase alone or the topoisomerase II inhibitor alone. Thus, this combination provides a tumor or cancer treatment with fewer side effects since a lower dosage of both ingedients may be administered.

19 Claims, No Drawings

OTHER PUBLICATIONS

E. Swain. Pharmaceutical and Medical Packagind New Aug. 1999, 4 pages.*
C. Monneret. Eur. J. Med. Chem. (2001), pp. 483-493.*
M. Jung. Curr. Med. Chem. (2001), pp. 1505-1511.*
G. Ranjgolikar, et al. Breast Cancer Res. Treat. (1998), pp. 29-38.*
Hidenori Nakajima, et al., "FR901228, a Potent Antitumor Antibiotic, Is a Novel Histone Deacetylase Inhibitor", Experimental Cell Research, vol. 241, 1998, pp. 126-133.
Khan W. Li, et al., "Total Synthesis of the Antitumor Depsipeptide FR-901-228", J. Am. Chem. Soc., vol. 118, No. 30, 1996, pp. 7237-7238.
Yasuhiko Kano, et al., "The combined effects of histone deacetylase inhibitor FK228 and other anticancer agents—in vitro consideration", The Japanese Journal of Clinical Hematology, vol. 43, No. 8, Aug. 30, 2002, p. 116 (with English abstract).
Hirotsugu Ueda, et al., "FR901228, a Novel Antitumor Bicyclic Depsipeptide Produced by Chromobacterium Violaceum No. 968", The Journal of Antibiotics, vol. 47, No. 3, 1994, pp. 315-323.
Hiroshi Kosugi, et al., "In vivo Effects of a Histone Deacetylase Inhibitor, FK228, on Human Acute Promyelocytic Leukemia in NOD/Shi-scid/scid Mice", Jpn. J. Cancer Res., vol. 92, May 2001, pp. 529-536.
Richard L. Piekarz, et al., "Inhibitor of histone deacetylation, depsipeptide (FR901228), in the treatment of peripheral and cutaneous T-cell lymphoma: a case report", BLOOD, vol. 98, No. 9, Nov. 1, 2001, pp. 2865-2868.
Yuka Sasakawa, et al., "Effects of FK228, a novel histone deacetylase inhibitor, on human lymphoma U-937 cells in vitro and in vivo", Biochemical Pharmacology, vol. 64, 2002, pp. 1079-1090.
Myoung Sook Kim, et al., "Inhibition of histone deacetylase increases topoisomerase inhibitors efficiency in cells clinically resistant to Top2 inhibitors", Proceedings of the American Association for Cancer Research, vol. 43, XP-001205058, Mar. 2002, pp. 510-511.
Mikhail V. Blagosklonny, et al., "Pretreatment with DNA-damaging agents permits selective killing of checkpoint-deficient cells by microtubule-active drugs", The Journal of Clinical Investigation, Feb. 2000, vol. 105, No. 4, pp. 533-539.
U.S. Appl. No. 10/546,285, filed May 31, 2006, Sasakawa, et al.

* cited by examiner

ANTITUMOR AGENT

TECHNICAL FIELD OF THE INVENTION

The present invention relates to a pharmaceutical composition comprising, in combination, a topoisomerase II inhibitor and a pharmaceutical agent that remarkably enhances an antitumor effect of the inhibitor, such as a histone deacetylase inhibitor, and methods of using such topoisomerase II inhibitors and histone deacetylase inhibitors.

BACKGROUND OF THE INVENTION

Generally, in chemotherapy of tumor, particularly malignant tumor, an exclusive administration of an antitumor agent rarely results in a desired antitumor effect. To enhance the effect, a multiple drug therapy using, in combination, 2, 3 or more drugs having different action mechanisms, has been employed in clinical situations. In this combination therapy, antitumor agents having different action mechanisms are combined 1) to decrease insensitive cell population, 2) to prevent or delay appearance of drug-resistance, 3) to disperse toxicity by the combination of pharmaceutical agents having different toxicities, and the like, thereby decreasing side effects and enhancing antitumor action. However, aimless combination of antitumor agents having different action mechanisms for combination therapy does not necessarily lead to an enhanced antitumor effect, and therefore, a combination effect afforded by the combination of antitumor agents exhibiting higher antitumor activities has been studied.

It has been reported that a compound represented by the formula (I)

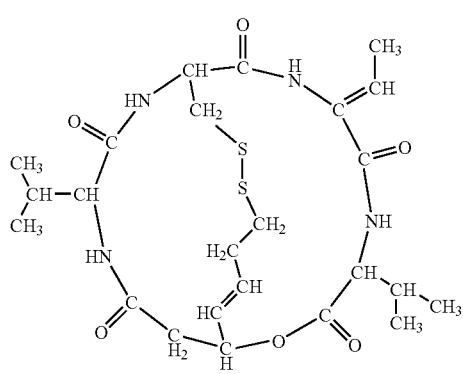

(I)

and a pharmaceutically acceptable salt thereof (hereinafter to be also referred to as compound A; SEQ ID; No 1), and particularly a stereoisomer of the formula (II)

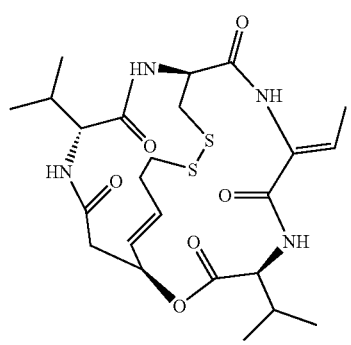

(II)

(hereinafter to be also referred to as FK228) and a pharmaceutically acceptable salt thereof strongly and selectively inhibit histone deacetylase to derive a potent antitumor activity, and that the substances cause high acetylation of histone in the treated cells, thereby inducing transcription-regulatory activity of various genes, cell cycle inhibitory activity and apoptosis (e.g., JP-B-7-64872, "Experimental Cell Research", US (1998), vol. 241, pp. 126-133).

However, there is no report as yet on the combined use of a histone deacetylase inhibitor such as Compound A and the like, and a topoisomerase II inhibitor, and the effect afforded by the combined use.

Histone deacetylase is a metallo-deacetylating enzyme coordinating Zn at an active center (M. S. Finnin et al., Nature, 401, 188-193 (1999)). This enzyme is considered to change affinity of various acetylated histones for DNA. The direct biological phenomenon brought thereby is a change in the chromatin structure. The minimum unit of the chromatin structure is a nucleosome wherein 146 bp DNA is wound 1.8 times anticlockwise around a histone octamer (H2A, H2B, H3 and H4, each 2 molecules, core histone). The core histone stabilizes the nucleosome structure by interaction of the positive charge of the N-terminus of each histone protein with DNA. Acetylation of histone is controlled by the equilibrium between an acetylation reaction involving histone acetyltransferase and a deacetylation reaction involving histone deacetylase. It is considered that the histone acetylation occurs at a lysine residue where the histone protein N-terminal is evolutionally preserved well, due to which a core histone protein loses charges at the N-terminal, interaction with DNA is attenuated, and the structure of nucleosome becomes unstable. Accordingly, the histone deacetylation is considered to be the reverse thereof, namely, a shift toward stabilization of the nucleosome structure. However, to what degree the acetylation changes the chromatin structure and how it relates to the transcriptional regulation etc. secondarily induced thereby are unclear in many aspects.

An object of the present invention is to provide an antitumor agent causing reduced side-effects and a superior antitumor activity based on the combined use of a topoisomerase II inhibitor as an antitumor agent, and a pharmaceutical agent that strikingly enhances an antitumor effect of the inhibitor.

SUMMARY OF THE INVENTION

The present inventors have conducted extensive studies, and as a result, have found that histone deacetylase inhibitors, particularly Compound A and FK228, remarkably enhance the antitumor effect of topoisomerase II inhibitors, and completed the present invention. Accordingly, the present invention includes the following:

[1] An antitumor agent comprising a combination of a histone deacetylase inhibitor and a topoisomerase II inhibitor, except amrubicin and a pharmaceutically acceptable salt thereof.

[2] The antitumor agent of [1] above, wherein the topoisomerase II inhibitor is at least one of an anthracycline anticancer drug or a pharmaceutically acceptable salt thereof, except amrubicin and a pharmaceutically acceptable salt thereof, etoposide, mitoxantrone, sobuzoxane, amsacrine, teniposide, and pharmaceutically acceptable salts thereof.

[3] The antitumor agent of [2] above, wherein the histone deacetylase inhibitor is Compound A, and the topoisomerase II inhibitor is an anthracycline anticancer drug or a pharmaceutically acceptable salt thereof, except amrubicin and a pharmaceutically acceptable salt thereof.

[4] The antitumor agent of [3] above, wherein the anthracycline anticancer drug or a pharmaceutically acceptable salt thereof is at least one of aclarubicin, idarubicin, epirubicin, daunorubicin, doxorubicin, pirarubicin, and pharmaceutically acceptable salts thereof.

[5] The antitumor agent of [1] to [4] above, which is used for lung cancer, malignant lymphoma, cancer of digestive organ, breast cancer, ovarian cancer, chondrosarcoma, bladder cancer, leukemia, kidney cancer or prostate cancer.

[6] An antitumor effect enhancer of a topoisomerase II inhibitor, except amrubicin and a pharmaceutically acceptable salt thereof, which comprises a histone deacetylase inhibitor as an active ingredient.

[7] The enhancer of [6] above, wherein the topoisomerase II inhibitor is at least one of an anthracycline anticancer drug or a pharmaceutically acceptable salt thereof, except amrubicin and a pharmaceutically acceptable salt thereof, etoposide, mitoxantrone, sobuzoxane, amsacrine, teniposide, and pharmaceutically acceptable salts thereof.

[8] The enhancer of [7] above, wherein the histone deacetylase inhibitor is Compound A, and the topoisomerase II inhibitor is an anthracycline anticancer drug or a pharmaceutically acceptable salt thereof, except amrubicin and a pharmaceutically acceptable salt thereof.

[9] The enhancer of [8] above, wherein the anthracycline anticancer drug or a pharmaceutically acceptable salt thereof is at least one of aclarubicin, idarubicin, epirubicin, daunorubicin, doxorubicin, pirarubicin, and pharmaceutically acceptable salts thereof.

[10] The enhancer of any of [6] to [9] above, which is used for lung cancer, malignant lymphoma, cancer of digestive organ, breast cancer, ovarian cancer, chondrosarcoma, bladder cancer, leukemia, kidney cancer or prostate cancer.

[11] A method for treating a cancer, which comprises administrating, to a mammal, a combination of an effective amount of a histone deacetylase inhibitor and an effective amount of a topoisomerase II inhibitor, except amrubicin and a pharmaceutically acceptable salt thereof.

[12] The method of [11] above, wherein the topoisomerase II inhibitor is at least one of an anthracycline anticancer drug or a pharmaceutically acceptable salt thereof, except amrubicin and a pharmaceutically acceptable salt thereof, etoposide, mitoxantrone, sobuzoxane, amsacrine, teniposide, and pharmaceutically acceptable salts thereof.

[13] The method of [12] above, wherein the histone deacetylase inhibitor is Compound A, and the topoisomerase II inhibitor is an anthracycline anticancer drug or a pharmaceutically acceptable salt thereof, except amrubicin and a pharmaceutically acceptable salt thereof.

[14] The method of [13] above, wherein the anthracycline anticancer drug or a pharmaceutically acceptable salt thereof is at least one of aclarubicin, idarubicin, epirubicin, daunorubicin, doxorubicin, pirarubicin, and pharmaceutically acceptable salts thereof.

[15] The method of any of [11] to [14] above, wherein the cancer is lung cancer, malignant lymphoma, cancer of digestive organ, breast cancer, ovarian cancer, chondrosarcoma, bladder cancer, leukemia, kidney cancer or prostate cancer.

[16] A method of enhancing an antitumor effect of a topoisomerase II inhibitor, except amrubicin and a pharmaceutically acceptable salt thereof, which comprises administrating an effective amount of a histone deacetylase inhibitor to a mammal.

[17] The method of [16] above, wherein the topoisomerase II inhibitor is at least one of an anthracycline anticancer drug or a pharmaceutically acceptable salt thereof, except amrubicin and a pharmaceutically acceptable salt thereof, etoposide, mitoxantrone, sobuzoxane, amsacrine, teniposide, and pharmaceutically acceptable salts thereof.

[18] The method of [17] above, wherein the histone deacetylase inhibitor is Compound A, and the topoisomerase II inhibitor is an anthracycline anticancer drug or a pharmaceutically acceptable salt thereof, except amrubicin and a pharmaceutically acceptable salt thereof.

[19] The method of [18] above, wherein the anthracycline anticancer drug or a pharmaceutically acceptable salt thereof is at least one of aclarubicin, idarubicin, epirubicin, daunorubicin, doxorubicin, pirarubicin, and pharmaceutically acceptable salts thereof.

[20] The method of any of [16] to [19] above, which enhances an antitumor effect against lung cancer, malignant lymphoma, cancer of digestive organ, breast cancer, ovarian cancer, chondrosarcoma, bladder cancer, leukemia, kidney cancer or prostate cancer.

[21] A pharmaceutical composition comprising, as active ingredients, a histone deacetylase inhibitor and a topoisomerase II inhibitor, except amrubicin and a pharmaceutically acceptable salt thereof.

[22] The pharmaceutical composition of [21] above, wherein the topoisomerase II inhibitor is at least one of an anthracycline anticancer drug or a pharmaceutically acceptable salt thereof, except amrubicin and a pharmaceutically acceptable salt thereof, etoposide, mitoxantrone, sobuzoxane, amsacrine, teniposide, and pharmaceutically acceptable salts thereof.

[23] The pharmaceutical composition of [22] above, wherein the histone deacetylase inhibitor is Compound A, and the topoisomerase II inhibitor is an anthracycline anticancer drug or a pharmaceutically acceptable salt thereof, except amrubicin and a pharmaceutically acceptable salt thereof.

[24] The pharmaceutical composition of [23] above, wherein the anthracycline anticancer drug or a pharmaceutically acceptable salt thereof is at least one of aclarubicin, idarubicin, epirubicin, daunorubicin, doxorubicin, pirarubicin, and pharmaceutically acceptable salts thereof.

[25] A commercial package comprising a combination drug containing a histone deacetylase inhibitor and a topoisomerase II inhibitor in combination, except amrubicin and a pharmaceutically acceptable salt thereof, and a written matter associated with the combination drug, the written matter stating that the combination drug can or should be used for an antitumor agent.

[26] The commercial package of [25] above, wherein the topoisomerase II inhibitor is at least one of an anthracycline anticancer drug or a pharmaceutically acceptable salt thereof, except amrubicin and a pharmaceutically acceptable salt thereof, etoposide, mitoxantrone, sobuzoxane, amsacrine, teniposide, and pharmaceutically acceptable salts thereof.

[27] The commercial package described in [26] above, wherein the histone deacetylase inhibitor is Compound A, and the topoisomerase II inhibitor is an anthracycline anticancer drug or a pharmaceutically acceptable salt thereof, except amrubicin and a pharmaceutically acceptable salt thereof.

[28] The commercial package of [27] above, wherein the anthracycline anticancer drug or a pharmaceutically acceptable salt thereof is at least one of aclarubicin, idarubicin, epirubicin, daunorubicin, doxorubicin, pirarubicin, and pharmaceutically acceptable salts thereof.

[29] A commercial package comprising a preparation containing a histone deacetylase inhibitor, and a written matter associated with therewith, the written matter stating that the preparation can or should be used for enhancing the antitumor effect of a topoisomerase II inhibitor, except amrubicin and a pharmaceutically acceptable salt thereof.

[30] The commercial package of [29] above, wherein the topoisomerase II inhibitor is at least one of an anthracycline anticancer drug or a pharmaceutically acceptable salt thereof, except amrubicin and a pharmaceutically acceptable salt thereof, etoposide, mitoxantrone, sobuzoxane, amsacrine, teniposide, and pharmaceutically acceptable salts thereof.

[31] The commercial package of [30] above, wherein the histone deacetylase inhibitor is Compound A, and the topoisomerase II inhibitor is an anthracycline anticancer drug or a pharmaceutically acceptable salt thereof, except amrubicin and a pharmaceutically acceptable salt thereof.

[32] The commercial package of [31] above, wherein the anthracycline anticancer drug or a pharmaceutically acceptable salt thereof is at least one of aclarubicin, idarubicin, epirubicin, daunorubicin, doxorubicin, pirarubicin, and pharmaceutically acceptable salts thereof.

DETAILED DESCRIPTION OF THE INVENTION

The "histone deacetylase inhibitor" or (HDAC inhibitors) in the present invention is a compound that binds to an active site of histone deacetylase competitively with substrates, or a compound that binds to a different site from active site of histone deacetylase to change the enzyme activity of histone deacetylase and/or decreases the enzymatic activity of histone deacetylase or otherwise inhibits enzyme activity. To be specific, the aforementioned Compound A, FK228, salts thereof and derivatives thereof (e.g., acetylated Compound A, thiol form with reduced S—S bond described in WO 02/06307, and prodrugs thereof) can be mentioned. Analogs of FK228 are described in U.S. Pat. No. 6,403,555. In addition, Trichostatin A, sodium butyrate, suberoylanilide hydroxamic acid (SAHA), MS-275, cyclic hydroxamic-acid-containing peptide, Apicidin, Trapoxin and the like are the compounds reported to have a histone deacetylase inhibitory activity. The inhibitors can be administered or used alone or in combination with one or more additional histone deacetylase inhibitors.

"Compound A" or "compound A", used interchangeably herein, includes its stereoisomers (e.g., FK 228) based on an asymmetric carbon atom or a double bond, such as an optically active form, a geometric isomer, racemic mixtures and the like.

Moreover, polymorphic forms, solvates (e.g., inclusion compounds (e.g., hydrate etc.)) and anhydrous forms of the compounds described herein, such as compound A, FK 228 and pharmaceutically acceptable salts thereof, are also encompassed in the scope of the present invention.

In the present specification, unless particularly specified, a simple reference to compound A includes any member of the group of compounds regardless of stereoisomerism, and includes FK 228 or pharmaceutically acceptable salt thereof.

The compound A or a salt thereof are known and available substances. For example, FK 228, which is one of the stereoisomers of compound A, can be obtained by culturing a strain belonging to the genus Chromobacterium, which is capable of producing FK 228, under aerobic conditions, and harvesting the substance from its culture broth. As the strain belonging to the genus Chromobacterium, which is capable of producing FK 228, for example, Chromobacterium violaceum WB968 (FERM BP-1968) can be mentioned. More specifically, FK 228 can be obtained from a FK 228 producing strain as described in JP-B-7-64872 (corresponding to U.S. Pat. No. 4,977,138, which is incorporated herein by reference). FK 228 is preferably harvested from a strain belonging to the genus Chromobacterium, which is capable of producing FK 228, because it can be obtained more easily. Synthetic or semi-synthetic FK 228 is also advantageous in that further purification step is not necessary or the number of steps can be reduced. Similarly, compounds A other than FK 228 can be also obtained by semi-synthesis or total synthesis by conventionally known methods. To be more specific, it can be produced according to the method reported by Khan W. Li, et al. (J. Am. Chem. Soc., Vol. 118, 7237-7238(1996)).

The form of a pharmaceutically acceptable salt of compound A, or other HDAC inhibitors, includes salts with a base or an acid addition salt such as salts with inorganic base (e.g., alkali metal salts such as sodium salt, potassium salt etc., alkaline earth metal salts such as calcium salt, magnesium salt etc., ammonium salt), salts with an organic base (e.g., organic amine salts such as triethylamine salt, diisopropylethylamine salt, pyridine salt, picoline salt, ethanolamine salt, triethanolamine salt, dicyclohexylamine salt, N,N'-dibenzylethylenediamine salt etc.), inorganic acid addition salts (e.g., hydrochloride, hydrobromide, sulfate, phosphate etc.), organic carboxylic acid or sulfonic acid addition salts (e.g., formate, acetate, trifluoroacetate, maleate, tartrate, fumarate, methanesulfonate, benzenesulfonate, toluenesulfonate etc.), salts with a basic or acidic amino acid (e.g., arginine, aspartic acid, glutamic acid etc.) and the like.

The "topoisomerase II inhibitor" in the present invention is a compound that binds to an active site of topoisomerase II competitively with substrates, or a compound that binds to a different site from active site of topoisomerase II to change the enzyme activity of topoisomerase II, and/or a compound that decreases the enzyme activity of topoisomerase II or otherwise inhibits enzyme activity. To be specific, anthracycline anticancer drugs, etoposide, mitoxantrone, sobuzoxane, amsacrine, teniposide and the like, and pharmaceutically acceptable salts thereof and combinations thereof can be mentioned.

The anthracycline anticancer drug or a pharmaceutically acceptable salt thereof, which is used as a topoisomerase II inhibitor in the present invention, is not particularly limited. Generally, amrubicin or a pharmaceutically acceptable salt thereof is not included in the scope of the present invention, which embodiment is described and claimed in copending application No. 334344/2003 filed in Japan on the same date as the patent application No. 334340/2003 filed in Japan forming the basis of this application. This copending application is incorporated herein by reference in its entirety. For example, aclarubicin, idarubicin, epirubicin, daunorubicin, doxorubicin (adriamycin), pirarubicin and the like, and pharmaceutically acceptable salts thereof can be mentioned, with preference given to doxorubicin, daunorubicin and pharmaceutically acceptable salts thereof. The anthracycline anticancer drug or a pharmaceutically acceptable salt thereof may be used alone or in a mixture of two or more kinds thereof.

In the present specification, the anthracycline anticancer drug or a pharmaceutically acceptable salt thereof is intended to exclude amrubicin and a pharmaceutically acceptable salt thereof, unless otherwise indicated.

As pharmaceutically acceptable salts of anthracycline anticancer drug, etoposide, mitoxantrone, sobuzoxane, amsacrine, teniposide and the like, salts with a base or an acid addition salt such as salts with inorganic base (e.g., alkali metal salts such as sodium salt, potassium salt etc., alkaline earth metal salts such as calcium salt, magnesium salt etc., ammonium salt), salts with an organic base (e.g., organic amine salts such as triethylamine salt, diisopropylethylamine salt, pyridine salt, picoline salt, ethanolamine salt, triethanolamine salt, dicyclohexylamine salt, N,N'-dibenzylethylenediamine salt etc.), inorganic acid addition salts (e.g., hydrochloride, hydrobromide, sulfate, phosphate etc.), organic carboxylic acid or sulfonic acid addition salts (e.g., formate, acetate, trifluoroacetate, maleate, tartrate, fumarate, methanesulfonate, benzenesulfonate, toluenesulfonate etc.), salts with a basic or acidic amino acid (e.g., arginine, aspartic acid, glutamic acid etc.) and the like can be mentioned.

In the present invention, the histone deacetylase inhibitor such as Compound A and the like, markedly enhances the antitumor activity of topoisomerase II inhibitor such as an anthracycline anticancer drug, a pharmaceutically acceptable salt thereof and the like. Thus, the antitumor agent and the antitumor effect enhancer of the present invention are useful as therapeutic drugs for cancer diseases including blood cancer and solid cancer, which are more specifically lung cancer, malignant lymphoma (e.g., reticulosarcoma, lymphosarcoma, Hodgkin's disease and the like), cancer of digestive organ (e.g., gastric cancer, gallbladder-bile duct cancer, pancreatic cancer, liver cancer, colon cancer, rectal cancer and the like), breast cancer, ovarian cancer, chondrosarcoma (e.g., osteosarcoma and the like), bladder cancer, leukemia (e.g., acute leukemia such as acute inversion of chronic myeloid leukemia and the like), kidney cancer, prostate cancer and the like.

The antitumor agent of the present invention is a combination of a histone deacetylase inhibitor and a topoisomerase II inhibitor (i.e., combination drug), and may be any as long as a histone deacetylase inhibitor and a topoisomerase II inhibitor can be combined when in use for the administration. Therefore, the antitumor agent of the present invention may be a single preparation obtained by simultaneously preparing a histone deacetylase inhibitor and a topoisomerase II inhibitor, or a combined preparation comprising two or more preparations obtained by separately processing a histone deacetylase inhibitor and a topoisomerase II inhibitor, as long as a histone deacetylase inhibitor and a topoisomerase II inhibitor can be combined when in use for the administration.

The form of administration is not particularly limited, and, for example, (1) administration of a composition comprising a histone deacetylase inhibitor and a topoisomerase II inhibitor, i.e., a single preparation, (2) simultaneous administration of two kinds of preparations obtained by separately processing the histone deacetylase inhibitor and the topoisomerase II inhibitor by the same administration route, (3) time staggered administration of two kinds of preparations obtained by separately processing a histone deacetylase inhibitor and a topoisomerase II inhibitor by the same administration route (e.g., administration in the order of a histone deacetylase inhibitor and a topoisomerase II inhibitor, or administration in reverse order), (4) simultaneous administration of two kinds of preparations obtained by separately processing a histone deacetylase inhibitor and a topoisomerase II inhibitor by different administration routes, and (5) time staggered administration of two kinds of preparations obtained by separately preparing a histone deacetylase inhibitor and a topoisomerase II inhibitor by different administration routes (e.g., administration in the order of a histone deacetylase inhibitor and a topoisomerase II inhibitor, or administration in reverse order) and the like can be mentioned.

In the case of the time staggered administration, moreover, it is preferred that a histone deacetylase inhibitor and a topoisomerase II inhibitor be co-present in the body for a time period necessary for the histone deacetylase inhibitor to reinforce the antitumor effect of the topoisomerase II inhibitor. As such, it is preferred that the second inhibitor is administered before the first inhibitor is cleared from the patient.

The enhancer of the present invention comprises a histone deacetylase inhibitor, and may be any as long as a histone deacetylase inhibitor and a topoisomerase II inhibitor can be combined when in use for the administration. Therefore, as long as a histone deacetylase inhibitor is contained, the enhancer of the present invention may contain a topoisomerase II inhibitor in a single preparation. When it does not contain a topoisomerase II inhibitor, a topoisomerase II inhibitor can be administered separately as a combination drug.

The form of administration is not particularly limited, and, for example, (1) administration of an enhancer of the present invention, comprising a histone deacetylase inhibitor and a topoisomerase II inhibitor in a single preparation, (2) simultaneous administration of the enhancer of the present invention and a topoisomerase II inhibitor by the same administration route, (3) time staggered administration of the enhancer of the present invention and a topoisomerase II inhibitor by the same administration route (e.g., administration in the order of a topoisomerase II inhibitor and the enhancer of the present invention, or administration in reverse order), (4) simultaneous administration of the enhancer of the present invention and a topoisomerase II inhibitor by different administration routes, and (5) time staggered administration of the enhancer of the present invention and a topoisomerase II inhibitor by different administration routes (e.g., administration in the order of a topoisomerase II inhibitor and the enhancer of the present invention, or administration in reverse order) and the like can be mentioned.

In addition, in the case of time staggered administration, both ingredients need to be co-present in the body as in the case of the above-mentioned antitumor agent.

In the present invention, the ratio of combination of the histone deacetylase inhibitor and the topoisomerase II inhibitor is generally in the range of 1:100 to 100:1, preferably in the range of 1:10 to 10:1, in a weight ratio, whether they are prepared into a single preparation or separate preparations.

To enhance the antitumor effect of the present invention, administration along with ATRA (all-trans-retinoic acid) and other antitumor agents is also possible (e.g., administration as a single preparation, or simultaneous or sequential administration as separate preparations). In addition, the invention includes administering additional active agents that can treat or prevent side effects of one or more of the antitumor agents being administered.

The antitumor agent of the present invention can be used in the form of a pharmaceutical preparation such as a solid, semisolid or liquid preparation (tablet, pellet, troche, capsule, suppository, cream, ointment, aerosol, powder, liquid, emulsion, suspension, syrup, injection etc.) containing a histone deacetylase inhibitor and/or topoisomerase II inhibitor as an active ingredient, which is suitable for transrectal, intranasal, pulmonary, vaginal, external (topical), oral or parenteral (including subcutaneous, implantation, intravenous and intramuscular) administration.

The antitumor effect enhancer of the present invention can be used in the form of a pharmaceutical preparation such as a solid, semisolid or liquid preparation (tablet, pellet, troche, capsule, suppository, cream, ointment, aerosol, powder, liquid, emulsion, suspension, syrup, injection etc.) containing a histone deacetylase inhibitor as an active ingredient, which is suitable for transrectal, intranasal, pulmonary, vaginal, external (topical), oral or parenteral (including subcutaneous, implantation, intravenous and intramuscular) administration.

The antitumor agent and antitumor effect enhancer of the present invention can be also produced by conventional methods using various organic or inorganic carriers conventionally used for forming pharmaceutical preparations, such as excipients (e.g., sucrose, starch, mannitol, sorbitol, lactose, glucose, cellulose, talc, calcium phosphate, calcium carbonate etc.), condensation agents (e.g., cellulose, methyl cellulose, hydroxypropyl cellulose, polypropylpyrrolidone, gelatin, gum arabic, polyethylene glycol, sucrose, starch etc.), disintegrants (e.g., starch, carboxymethyl cellulose, carboxymethyl cellulose calcium, hydroxypropyl starch, sodium starch glycolate, sodium hydrogen carbonate, calcium phosphate, calcium citrate etc.), lubricants (e.g., magnesium stearate, aerosil, talc, sodium lauryl sulfate etc.), corrigents (e.g., citric acid, menthol, glycine, orange powder etc.), preservatives (e.g., sodium benzoate, sodium hydrogen sulfite, methylparaben, propylparaben etc.), stabilizers (citric acid, sodium citrate, acetic acid etc.), suspensions (e.g., methyl cellulose, polyvinyl pyrrolidone, aluminum stearate etc.), dispersants (e.g., hydroxypropylmethyl cellulose etc.), diluents (e.g., water etc.), wax base materials (e.g., cacao butter, polyethylene glycol, white petrolatum etc.) and the like.

The antitumor agent and the antitumor effect enhancer of the present invention can be administered, without any particular limitation, in the form of the above-mentioned conventional pharmaceutical preparations, to mammals inclusive of human. Particularly, they are preferably administered intravenously, intramuscularly or orally.

The dose in the present invention can be set to a lower level, as compared to an exclusive administration of a histone deacetylase inhibitor or a topoisomerase II inhibitor.

For example, the dose is selected appropriately depending on various factors such as the body weight and/or age of patients, and/or the degree of the symptom and an administration route. For example, when Compound A was added as a histone deacetylase inhibitor, and an anthracycline anticancer drug or a pharmaceutically acceptable salt thereof was added as a topoisomerase II inhibitor, the dose of a combination of Compound A and an anthracycline anticancer drug or a pharmaceutically acceptable salt thereof for intravenous administration is generally in the range of 1 to 1000 mg/day/m$^2$ human body surface area, preferably in the range of 5 to 100 mg/day/m$^2$ human body surface area, and more preferably 10 to 60 mg/day/m$^2$ human body surface area by continuous drip infusion administration. In this case, the dose of Compound A is 0.1 to 100 mg/day/m$^2$ human body surface area, preferably 1 to 50 mg/day/m$^2$ human body surface area, and more preferably 5 to 30 mg/day/m$^2$ human body surface area, wherein the dose of the anthracycline anticancer drug or a pharmaceutically acceptable salt thereof to be administered is an amount obtained by subtracting the dose of Compound A from the combined dose of the above-mentioned Compound A and the anthracycline anticancer drug or the pharmaceutically acceptable salt thereof.

The present invention also provides a commercial package comprising a combination drug containing a histone deacetylase inhibitor and a topoisomerase II inhibitor in combination, except amrubicin and a pharmaceutically acceptable salt thereof, and a written matter associated with the combination drug, the written matter stating that the combination drug can or should be used for an antitumor agent; and a commercial package comprising a preparation containing a histone deacetylase inhibitor, and a written matter associated with the preparation, the written matter stating that the preparation can or should be used for enhancing the antitumor effect of a topoisomerase II inhibitor, except amrubicin and a pharmaceutically acceptable salt thereof.

EXAMPLES

To demonstrate the usefulness of the present invention, the results of a pharmacological test are shown in the following.

Experimental Method 1

For an animal, 6 to 12-week-old female CDF$_1$ mice (body weight: 17.2 to 24.7 g) were used at 5 to 12 mice per group. Furthermore, female DBA/2 mice were used for the subculture of tumor cells. For tumor, L-1210 mouse leukemia cells (hereinafter to be referred to as L-1210) were used. L-1210 cells subcultured intraperitoneally in DBA/2 mice were harvested and washed twice with a Hanks' solution. Dead cells were stained with trypan blue, viable cells were counted, and then the cells were suspended in a Hanks' solution, whereby the cells were adjusted to a predetermined number of cells. For the experiment, L-1210 cells ($1 \times 10^5$ cells) were implanted intraperitoneally into the CDF$_1$ mice.

The test compound was administered intraperitoneally into the mice once a day for 4 days, starting from the day after implantation of the tumor cells (dose: diluted test compound is administered at 10 ml/kg). In combined use experiment of the test compound, FK228 and the test compound were administered sequentially.

All the antitumor effects were evaluated using prolonged life of mice as an index.

For the survival period of the mice, the survival was observed over 30 days or 60 days after tumor implantation, a Median Survival Time (hereinafter to be referred to as MST) was determined and the life prolonging rate was calculated from the following formula:

$$\text{Life prolonging rate } [T/C\ (\%)] = \frac{MST \text{ of test compound administration group}}{MST \text{ of control group}} \times 100$$

The combination effect was determined by calculating a Combination Index (C.I.) from the following formula, wherein C.I.>1 was evaluated to be synergistic effect; C.I.=1 was evaluated to be addition effect; and C.I.<1 was evaluated to be no combination effect.

$$C.I. = \frac{T/C\ [\%]\ of\ FK228\ and\ the\ test\ compound\ combined\ use\ group - 100}{\left(\begin{array}{c}T/C\ [\%]\ of\ FK228\ alone\\group - 100\end{array}\right) + \left(\begin{array}{c}T/C\ [\%]\ of\ test\ compound\\alone\ group - 100\end{array}\right)}$$

Test Compound 1

Adriamycin was dissolved in distilled water, and diluted with physiological saline. Other test compounds were dissolved in physiological saline, and then diluted with physiological saline.

Test Results 1

The results are shown in Table 1.

TABLE 1

Combination effect by combined use 1 [6 mice per group (12 mice per group for control group)]

| Test compound | Dose (mg/mg) | T/C (%) | C.I. |
|---|---|---|---|
| FK228 + adriamycin | 0.14 + 0 | 100 | — |
| | 0 + 1 | 133 | — |
| | 0.14 + 1 | 178 | 2.36 |

The combined use of FK228 and adriamycin revealed a C.I. of 2.36, which was evaluated to suggest a synergistic effect. In addition, 2 mice out of 6 mice survived for 30 days.

As is clear from the results, the combined use of 0.14 mg/kg of FK228 ineffective by exclusive use and 1 mg/kg of adriamycin synergistically enhanced the antitumor effect thereof. Thus, FK228 is extremely useful as an antitumor effect enhancer.

| Formulation Example 1 | |
|---|---|
| FK228 | 20 mg |
| physiological saline | 4 ml |

FK228 (20 mg) is dissolved in and diluted with 4 ml of physiological saline to obtain a preparation for injection.

| Formulation Example 2 | |
|---|---|
| FK228 | 20 mg |
| doxorubicin hydrochloride | 10 mg |
| physiological saline | 4 ml |

FK228 (20 mg) and doxorubicin hydrochloride (10 mg) are dissolved in and diluted with 4 ml of physiological saline to obtain a preparation for injection.

A histone deacetylase inhibitor (particularly Compound A) remarkably enhances the antitumor effect of a topoisomerase II inhibitor.

Therefore, the antitumor agent of the present invention comprising a histone deacetylase inhibitor and a topoisomerase II inhibitor in combination provides higher cancer treatment effects with a lower dose as compared to an exclusive administration of a histone deacetylase inhibitor or a topoisomerase II inhibitor, and moreover, can decrease the side effects to a lower level.

This application is based on patent application Nos. 334340/2003 and 344315/2003 filed in Japan, the contents of which are hereby incorporated by reference.

While this invention has been shown and described with references to preferred embodiments thereof, it will be understood by those skilled in the art that various changes in form and details may be made therein without departing from the scope of the invention encompasses by the appended claims.

All patents, patent publications and other publications identified or referenced herein are incorporated by reference in their entirety.

SEQUENCE LISTING

```
<160> NUMBER OF SEQ ID NOS: 1

<210> SEQ ID NO 1
<211> LENGTH: 4
<212> TYPE: PRT
<213> ORGANISM: Chromobacterium sp.
<220> FEATURE:
<221> NAME/KEY: SITE
<222> LOCATION: (1)..(4)
<223> OTHER INFORMATION: In the formula COOHCH2CH(CHCHC2H4SH)OH, -COOH
      is bonded with the amino group of Val-1, -OH is bonded with the
      carboxylic group of Val-4, and -SH is bonded with the SH group of
      Cys-2 via a disulfide bond.
<220> FEATURE:
<221> NAME/KEY: MISC_FEATURE
<222> LOCATION: (3)..(3)
<223> OTHER INFORMATION: Xaa = any amino acid

<400> SEQUENCE: 1

Val Cys Xaa Val
1
```

What is claimed is:

1. A composition comprising:
a histone deacetylase inhibitor having formula (I) or a pharmaceutically acceptable salt thereof, and doxorubicin or a pharmaceutically acceptable salt thereof;
wherein said composition is formulated so as to exert a synergistic antitumor or anticancer activity in vivo;
wherein formula (I) is:

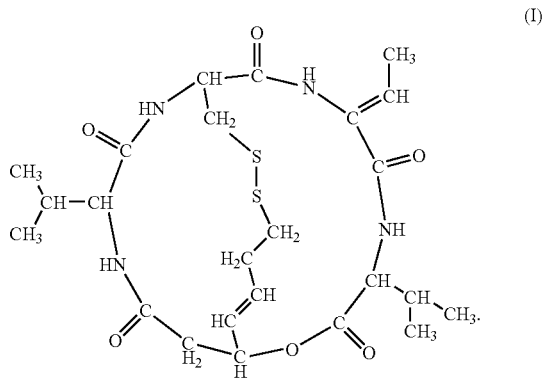

(I)

2. The composition of claim 1, which consists essentially of a histone deacetylase inhibitor having formula (I) and doxorubicin or pharmaceutically acceptable salt(s) thereof as the active anti-cancer ingredients.

3. The composition of claim 1, which consists of a histone deacetylase inhibitor having formula (I) and doxorubicin or pharmaceutically acceptable salt(s) thereof and at least one pharmaceutically acceptable carrier or excipient.

4. The composition of claim 1, wherein the histone deacetylase inhibitor comprises the FK228 stereoisomer or a salt thereof.

5. The composition of claim 1, wherein the histone deacetylase inhibitor of formula (I) and the doxorubicin, a topoisomerase II inhibitor, are present in a weight ratio ranging from 1:10 to 10:1.

6. The composition of claim 1, which is formulated for oral administration.

7. The composition of claim 1, Which is formulated for parenteral administration.

8. The composition of claim 1, which is formulated for intranasal, pulmonary, vaginal, or transrectal administration.

9. The composition of claim 1, Which is formulated For topical or external administration.

10. A commercial package comprising the composition of claim 1, and written matter indicating that said composition can or should be used to treat cancer or tumors.

11. A method for treating cancer or a tumor comprising:
administering to a subject in need thereof an effective amount of the composition of claim 1;
wherein said cancer or tumor is susceptible to treatment with a histone deacetylase inhibitor or a topoisomerase inhibitor, or both.

12. The method of claim 11, wherein said cancer or tumor is selected from the group consisting of lung cancer, malignant lymphoma, cancer of digestive organ, breast cancer, ovarian cancer, chondrosarcoma, bladder cancer, leukemia, kidney cancer and prostate cancer.

13. The method of claim 11, wherein the histone deacetylase inhibitor comprises the FK228 stereoisomer or a salt thereof.

14. The method of claim 11, which comprises administering FK228 and doxorubicin (adriamycin) or salt(s) thereof.

15. The method of claim 11, wherein the histone deacetylase inhibitor of formula (I) and doxorubicin or salt(s) thereof are present ma weight ratio ranging from 1:10 to 10:1.

16. The method of claim 11, comprising orally administering said composition.

17. The method of claim 11 comprising parenterally administering said composition.

18. The method of claim 11, comprising intranasally, pulmonarily, vaginally, or transrectally administering said composition.

19. The method of claim 11, comprising topically or externally administering said composition.

* * * * *